United States Patent [19]

Dean et al.

[11] 4,450,236

[45] May 22, 1984

[54] ASPOROGENIC MUTANT OF BACILLUS SUBTILIS USEFUL AS A HOST IN A HOST-VECTOR SYSTEM

[75] Inventors: Donald H. Dean, Worthington; Daniel M. Ellis, Columbus, both of Ohio

[73] Assignee: CPC International Inc., Englewood Cliffs, N.J.

[21] Appl. No.: 370,239

[22] Filed: Apr. 21, 1982

[51] Int. Cl.³ .................. C12N 1/20; C12N 15/00; C12R 1/25
[52] U.S. Cl. .................. 435/253; 435/172.1; 435/839; 935/74; 935/58
[58] Field of Search .................. 435/172, 253, 839

[56] References Cited

U.S. PATENT DOCUMENTS 4,237,224 12/1980 Cohen et al. .................. 435/170
4,302,544 11/1981 Young et al. .................. 435/253

OTHER PUBLICATIONS

Ellis, D. M. and Dean, D. H., Recombinant DNA Technical Bulletin, vol. 4, No. 1, Mar. 1981.
Burke, W. F. and Le, H. T., Recombinant DNA Technical Bulletin, vol. 3, No. 1, Dec. 1980.
Dedonder, et al, Applied and Environmental Microbiology, 33, 989–993, (1977).
Farmer and Rothman, J. Bacteriology, 89, 262–263, (1965).

Primary Examiner—Jerome D. Goldberg
Assistant Examiner—Kathleen S. McCowin
Attorney, Agent, or Firm—Stanley M. Parmerter

[57] ABSTRACT

A biologically pure strain of asporogenous *B. subtilis* DE101 (ATCC 39,095) is provided. This strain, which shows a low frequency of reversion to spore formers, is suitable for a host providing a high level of biological containment in a host-vector system for use in recombinant DNA methodology.

2 Claims, No Drawings

ASPOROGENIC MUTANT OF *BACILLUS SUBTILIS* USEFUL AS A HOST IN A HOST-VECTOR SYSTEM

FIELD OF THE INVENTION

This invention relates to a new mutant of *Bacillus subtilis* useful as a host in a host-vector system into which vectors containing various genes can be inserted using recombinant DNA methodology.

BACKGROUND OF THE INVENTION

Most genetic material in a bacterium exists as gaint DNA molecules which are present as the chromosome of the cell. A certain amount of the genetic material may also be present in the form of smaller, closed circular DNA molecules known as plasmids. The portion of the DNA molecule related to a specific hereditary trait is called a gene.

By techniques referred to as genetic engineering, it is possible to transfer a gene, which codes for the production of a specific protein, from one microorganism to another. The microorganism which receives the new genetic material is referred to as the host. Various workers have used these techniques to provide microorganisms which are superior producers of certain specific proteins such as enzymes.

It has been discovered that plasmids, which contain a series of genes linked together in the form of a circle, can be removed from the cells of one microorganism and inserted into the cells of another microorganism with comparative ease. Plasmids can also be used as vectors to carry new genetic material into a host organism. This is accomplished by first cutting the plasmid with an enzyme, known as a restriction endonuclease, that opens the circle of DNA. A fragment of foreign DNA, containing the desired gene, is inserted into the place where the DNA circle was cut. The circle is reformed by treatment with DNA ligase. The recombined plasmid, a new circular DNA molecule, contains the genes of the original plasmid plus the new gene from the piece of DNA which was inserted. This plasmid can be introduced into a host microorganism. The plasmid containing the new gene is then reproduced in the host microorganism and becomes part of its genetic material.

For a host microorganism to be suitable for use in genetic engineering, it must be capable of incorporating the new DNA. Furthermore, it must yield a viable microorganism which expresses the traits coded in the newly inserted gene. For the microorganism to produce useful quantities of protein, the microorganism must also be one that can be grown on a commercial scale.

Experimenters using the new recombinant DNA technology have been concerned that the microorganisms with new genetic material might produce substances harmful to man, animals or plants. Because of this concern, the National Institute of Health (NIH) issued "Guidelines for Research Involving Recombinant DNA Molecules" in 1978. These guidelines provided for various levels of physical containment in laboratories where genetic engineering experiments are conducted. They also established levels of biological containment for microorganisms containing recombinant DNA.

Biological containment relates to the use of host cells and vectors which have limited ability to survive if they escape from the laboratories into the natural environment. The NIH guidelines establish levels of biological containment for host-vector systems (hereafter designated HV) depending on the microorganisms and the genetic material used. HV1 is defined as a "host-vector system which provides a moderate level of containment". A high level of biological containment is required for a HV2 host-vector system.

The NIH has certified two mutants of *B. subtilis* for use as host components of HV1 systems. One of these, RUB331, is disclosed in U.S. Pat. No. 4,302,544, the disclosure of which is incorporated herein by reference in its entirety. The second of these is BGSC No. 1S53 which is described by Ellis, D. M. and Dean, D. H., Recombinant DNA Technical Bulletin, Vol. 4, No. 1, March, 1981. The NIH has approved one *B. subtilis* host component for a HV2 system. This strain, known as ASB298, is described by Burke, W. F. and Le, H. T., Recombinant DNA Technical Bulletin, Vol. 3, No. 1, December, 1980.

The present invention describes a new asporogenous mutant designated as *B. subtilis* DE101 (ATCC 39,095) useful as a host in a host-vector system. Although the mutant has limited ability to survive in the natural environment, it can be grown on a commercial scale. Since the mutant does not require an antibiotic for growth, it is a more practical host for enzyme production than the approved HV2 host, ASB298, which grows in the presence of streptomycin.

SUMMARY OF THE INVENTION

In accordance with this invention, there is provided a biologically pure culture of asporogenous *B. subtilis* DE101 (ATCC 39,095) suitable for use as a host component in a host-vector system characterized in that it has a frequency of reversion to spore formers of less than about $10^{-7}$ when grown under conditions of aeration and having the following genetic markers: thy A1, thy B1, pyr D1, and spo OAΔ677.

In addition, there is provided a biologically pure culture of asporogenous *B. subtilis* DE2 (ATCC 39,092) useful as an intermediate for the preparation of asporogenous host components of host-vector systems characterized in that it contains the following genetic markers: pyr D1 and spo OAΔ677.

DETAILED DESCRIPTION OF THE INVENTION

The *B. subtilis* strains disclosed and claimed were prepared by incorporating the genetic material from previously reported strains of *B. subtilis*. The parent strain, 1A6, was described by Dedonder, et al, Applied and Environmental Microbiology, 33, 989–993 (1977). It is available from the American Type Culture Collection, Rockville, Md. as ATCC 39,085. *B. subtilis* Strain 1S53 was reported by Ellis and Dean, Recombinant DNA Technical Bulletin, 4, 1–3 (1981). It is available from the American Type Culture Collection as ATCC 39,090. Strain 1A243, ATCC 39,087, was described by Farmer and Rothman, J. Bacteriology, 89, 262–263 (1965) and originally called 168 thy−, ind−.

The first step in the preparation of DE101 involved transfer of the asporogenous characteristic of Strain 1S53 into the parental strain, 1A6, by a transformation reaction. The resultant transformant, although initially unstable for auxotrophic markers, soon reverted to a stable mutant which is designated as DE2. This mutant is asporogenous and is useful as an intermediate in forming other asporogenous mutants.

A portion of the DNA from *B. subtilis* Strain 1A243 was then transferred into DE2 using a transduction process by means of the phage PBS1. A stable mutant, DE101, possessing the markers: thy A1, thy B1, pyr D1, and spo OAΔ677, resulted.

The asporogenous strain of the present invention shows a frequency of reversion to spore formers of less than about $10^{-7}$. It is able to grow under industrial conditions not requiring expensive growth requirements. It has a low survival rate under natural or escape conditions and a very low tendency to transmit plasmids to other organisms by natural genetic transfer. Although the organism shows a low degree of competence when subjected to classical transformation techniques, excellent transformation with plasmids has been achieved using a protoplast transformation procedure. It functions well as a host for various plasmid vectors making it a useful strain to use as a host component of a *B. subtilis* host-vector system.

A detailed genetic map of the *B. subtilis* chromosome has been published by Henner and Hoch, Microbiological Reviews, 44, 57-82 (1980). Brief descriptions of the genetic markers mentioned in the disclosure of this invention follow:

(1) thy A1, thy B1: These mutations are in genes for two different thymidylate synthetases in *B. subtilis*. Both must be present to confer requirement for thymine and thymidine. This requirement reduces the ability of the host to survive in nature. The thy A1 mutation also gives trimethoprim resistance, a useful marker for identifying a host.

(2) trp C2: This mutation resides in the indol-3-glycerolphosphate gene, encoding an essential enzyme in the biosynthesis of the amino acid tryptophan. When deprived of tryptophan, not commonly found in nature as the free amino acid, strains carrying this mutation cease to grow.

(3) pry D1: This mutation prevents formation of an enzyme essential to the production of pyrimidine by the microorganism. Since pyrimidines are essential precursors of DNA and RNA and are not commonly found in nature, starvation for pyrimidines will affect the growth of the host and the production of plasmid vehicles introduced into the host.

(4) spo OAΔ677: This is a deletion mutation causing a block in the earliest stages of sporulation. This mutation destroys the ability of the Bacillus to form spores, the form in which it normally survives in nature when subjected to heat, ultraviolet light, chemicals and desiccation.

(5) ilv A1: Mutants containing this marker require both isoleucine and valine for growth.

The following example illustrates certain embodiments of the present invention. Unless otherwise stated, all proportions and percentages are provided on the basis of weight. All strains bearing ATCC numbers are available from the Americal Type Culture Collection, Rockville, Md. All reagents bearing the Difco name are available from the Difco Laboratories, Detroit, Mich.

EXAMPLE

Transformation of the parent spore-forming *B. subtilis* Strain 1A6 (thy A1, thy B1, trp C2, ilv A1, pyr D1) into an asporogenous strain by incorporation of DNA obtained from *B. subtilis* 1S53 (spo OAΔ677) was carried out as follows:

*B. subtilis* 1A6 (ATCC 39,085) was grown overnight on agar plates containing Spizizen's minimal medium. Spizizen's minimal medium is a solution of (a) ammonium sulfate—0.2%; (b) potassium phosphate (dibasic)—1.4%; (c) potassium phosphate (monobasic)—0.6%; (d) sodium citrate—0.1%; and (e) magnesium sulfate—0.02%; pH adjusted to 7.4. Cells from these plates were inoculated into 30 ml of a solution prepared by adding 0.1 ml 10% $MgSO_4$, 1.2 ml 50% glucose, 1.0 ml 10% Difco yeast extract and 1.0 ml 2% Difco casein hydrolyzate to 99 ml of Spizizen's minimal medium. The flask was incubated at 37° C. and shaken at 200 rpm. The increase in optical density was monitored using a Klett spectrophotometer with a red filter. When cultures reached the transition between log and stationary growth (change in optical density of less than 5% in 15 minutes), they were diluted into 100 ml of the growth medium to which had been added 1.0 ml of 0.05 M $CaCl_2$ and 2.0 ml of 0.1 M $MgCl_2$. The mixture was incubated for an additional 90 minutes before donor DNA was added.

Donor DNA was obtained from *B. subtilis* 1S53 (ATCC 39,090) by the following procedure.

Strain 1S53 was grown overnight at 37° C. in a Heart Infusion Broth (BHI) medium available from Difco Laboratories, Detroit, Mich. The mixture was diluted with 500 ml of fresh BHI medium and grown at 37° C. until the optical density of the mixture measured at 660 nanometers was 0.6. The cells were collected by centrifugation and resuspended in 10 ml of a solution containing 0.03 M tris(hydroxymethyl)aminomethane at pH 8.0, 0.005 M ethylenediamine tetraacetic acid and 0.05 M NaCl, and mixed with 4 mg of lysozyme. The cells were shaken gently (100 rpm) for 20 minutes at 37° C. Then 80 μl of pronase (10 mg/ml) was added and incubation was continued for another 60 minutes. The cells were then lysed by the addition of 1.0 ml of 20% sodium dodecyl sulfate solution. The lysate was extracted with phenol, phenol-chloroform, and chloroform, retaining the aqueous layer each time. DNA was precipitated by the addition of 3 volumes of cold 95% ethanol. The precipitated DNA was collected and resuspended in a solution containing 0.15 M NaCl and 0.015 sodium acetate at pH 7, and incubated at 37° C. for 1 hour with a mixture of 1 mg pancreatic ribonuclease (type 1A from Bovine Pancreas, available from Sigma Chemical Company, St. Louis, Mo.) and 5 units of Ribonuclease T1 (Grade IV from *Aspergillus oryzae*, Sigma Chemical Company). The mixture was then re-extracted with phenol, phenol-chloroform, and chloroform and reprecipitated with ethanol. The DNA was redissolved in a solution containing 0.015 M sodium chloride and 0.0015 sodium acetate at pH 7, dialyzed against 3 changes of a large volume of the same solution during a 24-hour period before it was used for transformation.

The competent cells of *B. subtilis* 1A6, prepared as described above, were mixed with DNA at a concentration of 10 μg/ml of final mixture and the culture was shaken gently (100 rpm) for 60 minutes at 37° C. The culture was then diluted with 10 volumes of BHI and allowed to grow for an additional 3 hours at 37° C. The cells were collected by centrifugation, washed once with distilled water and spread on plates containing agar with Spizizen's minimal medium plus thymine (50 μg/ml), tryptophan (20 μg/ml) and uracil (20 μg/ml). The colonies which grew were screened for asporogenous mutants.

Three screening tests were applied to test for asporogenous mutants. First, the cells must remain unpigmented when grown on DSM plates (Sononshein, et al, J. Bacteriology, 120, 253–265 (1974). In contrast, spore-forming cells developed a dark reddish-brown color after 3 days' growth on these plates. DSM is Difco Sporulation Medium containing 0.8% nutrient broth, 0.025% $MgSO_4 \cdot 7H_2O$, 0.1% KCl, $1 \times 10^{-6}$M $FeSO_4$, $1 \times 10^{-5}$ M $MnCl_2$ and $1 \times 10^{-3}$ M $CaCl_2$. Secondly, if spores are present in the culture, they appear as phase-bright bodies in individual cells under a phase microscope. In contrast, asporogenous strains fail to develop the phase-bright stage. In the third test, the spores that are present in the culture, survive a heat treatment of 60° C. for 20 minutes. In contrast, all cells in the culture of an asporogenous strain are susceptible to killing by heat in this test. For a strain to be classified as asporogenous, it must pass all three of the screening tests. One individual colony which passed these screening tests was not at first stable for auxotrophic markers but reverted to a stable mutant having the markers: pyr D1 and spo OA$\Delta$677. It was designated as DE2.

Strain DE2 (pyr D1, spo OA$\Delta$677) was converted into the instant asporogenous strain DE101 by transduction with phage PBS1 using DNA from a donor strain of *B. subtilis* 1A243 (trp C2, thy A1, thy B1), available as ATCC 39,087. Transduction was carried out by the method of Young and Wilson, Handbook of Genetics, Vol. 1, pp. 69–78, Plenum Press, New York, 1974, except that no chloramphenicol was added. Cells were selected from trimethoprim resistance by the method described by Neuhardt, et al, Proc. Natl. Acad. Sci., U.S., 75, 1194–1198 (1978). A biologically pure strain obtained by this process was designated as DE101. It has the genetic markers: thy A1, thy B1, pyr D1, and spo OA$\Delta$677. Strain DE101 is available from the American Type Culture Collection as ATCC 39,095.

DE101 requires mineral salts containing ammonium, potassium, phosphate and sodium ions for growth. It will utilize various carbon sources including glucose. Thymine or thymidine, and pyrimidines are required for growth. Corn steep liquor can be used as the source of these requirements but the addition of thymine to this liquor enhances growth of the organism.

Stability of the auxotrophic markers in Strain DE101 to reversion was determined by the following method. The strain was grown overnight at 37° C. in Spizizen's minimal medium which was supplemented with 0.1% glucose, 10 $\mu$g/ml of uracil, and 50 $\mu$g/ml of thymine. Cultures were transferred to fresh media and allowed to grow for 6 hours with shaking at 37° C. The cells were then collected by centrifugation, washed twice in water, resuspended in water and titered on agar plates containing the minimal medium lacking only one of the requirements. Total viable cells were determined as colony-forming units (CFU) on minimal plates containing all requirements. All determinations were done in triplicate. The data in table I show the stability of the auxotrophic markers in the strain.

TABLE I

| REVERSION FREQUENCIES OF MUTATIONS IN DE101 | | | |
|---|---|---|---|
| Mutation | CFU/ml (V) | Revertants/ml (R) | R/V |
| thy A1, thy B1 | $2.6 \pm 0.019 \times 10^7$ | 0 | $<10^{-7}$ |
| pyr D1 | $2.6 \pm 0.019 \times 10^7$ | $1.67 \pm 0.30$ | $6.4 \times 10^7$ |

Strain DE101 does not revert to spore formers even under conditions of adequate aeration which allow the cells the fullest possibility to sporulate. Cells were grown in DSM (Difco) medium supplemented with 50 $\mu$g/ml thymine at 37° C. with shaking at 200 rpm. At 24-hour intervals, aliquots were removed and heated at 60° C. for 20 minutes. The heated samples were then titered to determine the number of survivors. Comparisons were made with the number of CFU/ml developed when unheated samples were titered. The results shown in Table II indicate that no heat-resistant cells could be recovered from DE101 grown under these optimized sporulation conditions.

TABLE II

| FORMATION OF HEAT-RESISTANT CELLS (SPORE FORMATION) of DE101 | | |
|---|---|---|
| Days | CFU/ml | Spores |
| 1 | $3.2 \times 10^8$ | 0 |
| 2 | $7.5 \times 10^7$ | 0 |
| 3 | $2.5 \times 10^8$ | 0 |

Survival of DE101 in liquids was assessed as follows. Mid-log cultures were used to inoculate samples of BHI, Spizizen's minimal medium plus 0.1% glucose and sterile distilled water. One-ml samples were placed in capped 15-ml test tubes which were shaken in a 30° C. air bath. At 24-hour intervals, 3 tubes from each group were removed and titered for survivors. The results expressed in CFU/ml are given in Table III.

TABLE III

| SURVIVAL OF DE101 IN LIQUID MEDIA | | | |
|---|---|---|---|
| Time (days) | BHI CFU/ml | Minimal Medium CFU/ml | $H_2O$ CFU/ml |
| 0 | $7.0 \pm 1.2 \times 10^5$ | $4.3 \pm 0.3 \times 10^5$ | $4.7 \pm 0.9 \times 10^5$ |
| 1 | 0 | 10 | 0 |
| 2 | 0 | 0 | 0 |

To assess the survivability of DE101 in a simulated laboratory bench-top spill, 0.25-inch diameter sterile concentration discs were saturated with an aqueous suspension of washed cells which have been grown to mid-log phase in BHI plus thymine. Discs were stored at 37° C. in sterile petri dishes. At 24-hour intervals, 3 discs were rehydrated in 10 ml Spizizen's minimal medium and the sample was titered for survivors. The results expressed in CFU/ml given in Table IV are the average of counts made on 3 separate discs.

TABLE IV

| SURVIVAL OF DE101 ON "BENCH TOP" | | |
|---|---|---|
| Time (days) | CFU/ml | Survival (%) |
| 0 | $7.7 \pm 2.0 \times 10^5$ | 100 |
| 1 | $6.0 \pm 3.6 \times 10^1$ | $8 \times 10^{-3}$ |
| 2 | 0 | 0 |
| 3 | 0 | 0 |

As shown in Table IV, DE101 survives for only a short time under these conditions of desiccation. This furnishes additional evidence of its suitability for use as a biological containment host for recombinant DNA.

The work described herein was all done in conformity with physical and biological containment requirements specified in the NIH guidelines.

What is claimed is:

1. A biologically pure culture of asporogenous *B. subtilis* DE101 (ATCC 39,095) suitable for use as a host component in a host-vector system characterized in that it has a frequency of reversion to spore formers of less than about $10^{-7}$ when grown under conditions of aeration and having the following genetic markers: thy A1, thy B1, pyr D1, and spo OA$\Delta$677.

2. A biologically pure culture of asporogenous *B. subtillis* DE2 (ATCC 39,092) useful as an intermediate for preparation of asporogenous host components of host-vector systems characterized in that it contains the following genetic markers: pyr D1 and spo OA$\Delta$677.

* * * * *